US012670995B2

(12) United States Patent
Akikawa et al.

(10) Patent No.: US 12,670,995 B2
(45) Date of Patent: Jun. 30, 2026

(54) INFORMATION PROCESSING APPARATUS, CLINICAL DIAGNOSIS SYSTEM, AND PROGRAM

(71) Applicant: Hitachi High-Tech Corporation, Tokyo (JP)

(72) Inventors: Ryota Akikawa, Tokyo (JP); Manabu Andou, Tokyo (JP); Katsuyuki Okeya, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 51 days.

(21) Appl. No.: 18/579,921

(22) PCT Filed: Jun. 15, 2022

(86) PCT No.: PCT/JP2022/023889
§ 371 (c)(1),
(2) Date: Jan. 17, 2024

(87) PCT Pub. No.: WO2023/021822
PCT Pub. Date: Feb. 23, 2023

(65) Prior Publication Data

US 2024/0355478 A1 Oct. 24, 2024

(30) Foreign Application Priority Data

Aug. 19, 2021 (JP) ................................ 2021-134068

(51) Int. Cl.
*G16H 50/20* (2018.01)
*G16H 50/30* (2018.01)

(52) U.S. Cl.
CPC ............ *G16H 50/30* (2018.01); *G16H 50/20* (2018.01)

(58) Field of Classification Search
CPC ........ G16H 40/67; G16H 50/30; G16H 50/20; G16H 10/60
(Continued)

(56) References Cited

U.S. PATENT DOCUMENTS

2010/0105989 A1* 4/2010 Inokuchi ............... G16H 10/60 600/300
2016/0321414 A1 11/2016 Salganicoff et al.
(Continued)

FOREIGN PATENT DOCUMENTS

JP 2014106776 A * 6/2014
JP 2014186669 A * 10/2014
(Continued)

OTHER PUBLICATIONS

International Search Report of PCT/JP2022/023889 dated Sep. 6, 2022.
(Continued)

*Primary Examiner* — Alaaeldin M. Elshaer
(74) *Attorney, Agent, or Firm* — MATTINGLY & MALUR, PC

(57) ABSTRACT

An object of the present invention is to provide an information processing apparatus in which an overview of examinations required until confirmation of a disease can be grasped. An information processing apparatus according to the present invention includes: an information acquisition unit that acquires patient information; an examination planning unit that specifies an examination item to be executed based on the patient information acquired by the information acquisition unit; and an output unit that outputs the examination item specified by the examination planning unit, in which the output unit outputs a plurality of examination items required until a disease can be confirmed or denied together with execution timings.

7 Claims, 9 Drawing Sheets

(58) Field of Classification Search
USPC ........................................................ 705/2, 3
See application file for complete search history.

(56) References Cited

U.S. PATENT DOCUMENTS

| | | | | |
|---|---|---|---|---|
| 2018/0096739 | A1* | 4/2018 | Sano | G06F 16/316 |
| 2019/0065688 | A1 | 2/2019 | Lee et al. | |
| 2020/0251215 | A1* | 8/2020 | Nemoto | G16H 50/20 |
| 2021/0035688 | A1* | 2/2021 | Ohyu | G06Q 10/02 |

FOREIGN PATENT DOCUMENTS

| | | | | |
|---|---|---|---|---|
| JP | 2017-21511 | A | | 1/2017 |
| JP | 2018206095 | A | * | 12/2018 |
| JP | 2020-126284 | A | | 8/2020 |
| JP | 2021-26447 | A | | 2/2021 |

OTHER PUBLICATIONS

International Preliminary Report on Patentability PCT/JP2022/023889 dated Sep. 5, 2023.
Extended European Search Report received in corresponding European Application No. 22858146.8 dated Jul. 11, 2025.
Kim, Y. et al., "DiagTree: Diagnostic Tree for Differential Diagnosis", Proceedings of The 2017 ACM On Conference On Information and Knowledge Management, New York, New York, Nov. 6-10, 2017, pp. 1179-1188.

* cited by examiner

[FIG. 1]
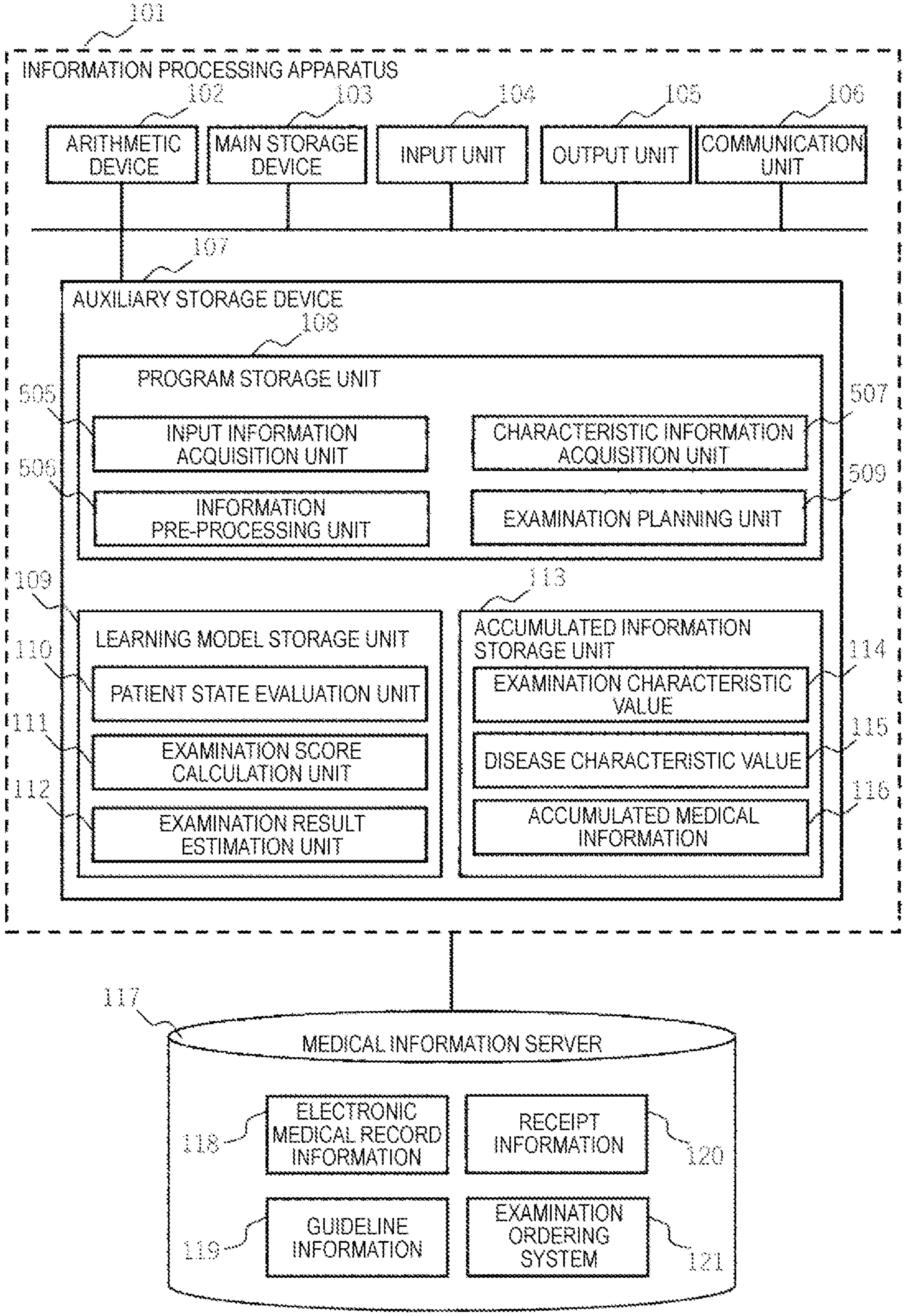

| PATIENT NUMBER | CONFIRMED DIAGNOSIS | EXAMINATION | | | | | | |
|---|---|---|---|---|---|---|---|---|
| | | EXAMINATION A | | | EXAMINATION B | | | · · |
| | | DATE | ITEM | RESULT | DATE | ITEM | RESULT | |
| 1 | DISEASE A | 2020/1/1 13:00 | EXAMINATION A | SYMPTOM A | 2020/1/2 14:00 | EXAMINATION A | SYMPTOM A | |
| 2 | DISEASE B | 2020/1/3 09:00 | EXAMINATION B | 37 | 2020/1/3 10:00 | EXAMINATION C | + | |
| 3 | DISEASE C | 2020/2/1 10:00 | EXAMINATION C | + | 2020/2/5 10:00 | EXAMINATION D | 4500 | |

| EXAMINATION ITEM | REFERENCE VALUE | COST | POSITIVE LIKELIHOOD RATIO | | | NEGATIVE LIKELIHOOD RATIO | | |
|---|---|---|---|---|---|---|---|---|
| | | | DISEASE A | DISEASE B | · · | DISEASE A | DISEASE B | · · |
| EXAMINATION A | 36.0 ~ 37.0 | - | 2.0 | 2.1 | | 0.7 | 0.38 | |
| EXAMINATION B | 400 ~ 900 | 21 | 1.2 | 6.6 | | 0.6 | 0.16 | |
| EXAMINATION C | ~ 130 | 200 | - | 1.2 | | - | 0.7 | |
| EXAMINATION D | - | 530 | 10.2 | 30 | | 0.22 | 0.1 | |

[FIG. 4]
| 401 | 402 | 403 | 404 | 405 | 406 |
|---|---|---|---|---|---|
| DISEASE NAME | CONDITION | PRETEST PROBABILITY | EXAMINATION THRESHOLD | TREATMENT THRESHOLD | RISK SCORE |
| DISEASE A | CONDITION A | 0.1 | 5 | 40 | 12 |
| | ⋮ | | | | |
| DISEASE B | CONDITION A | 0.01 | 30 | 80 | 93 |
| | ⋮ | | | | |
[FIG. 5]
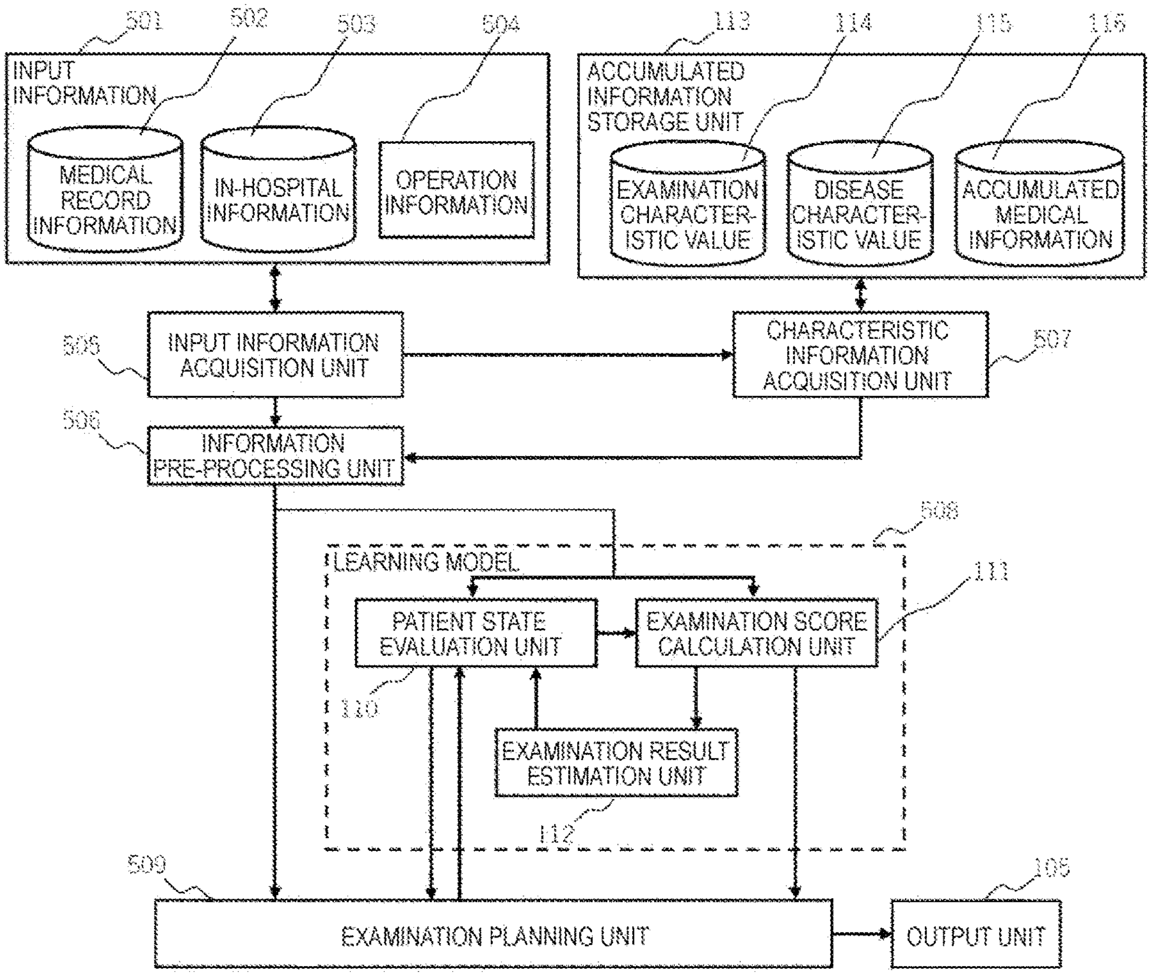

[FIG. 6]
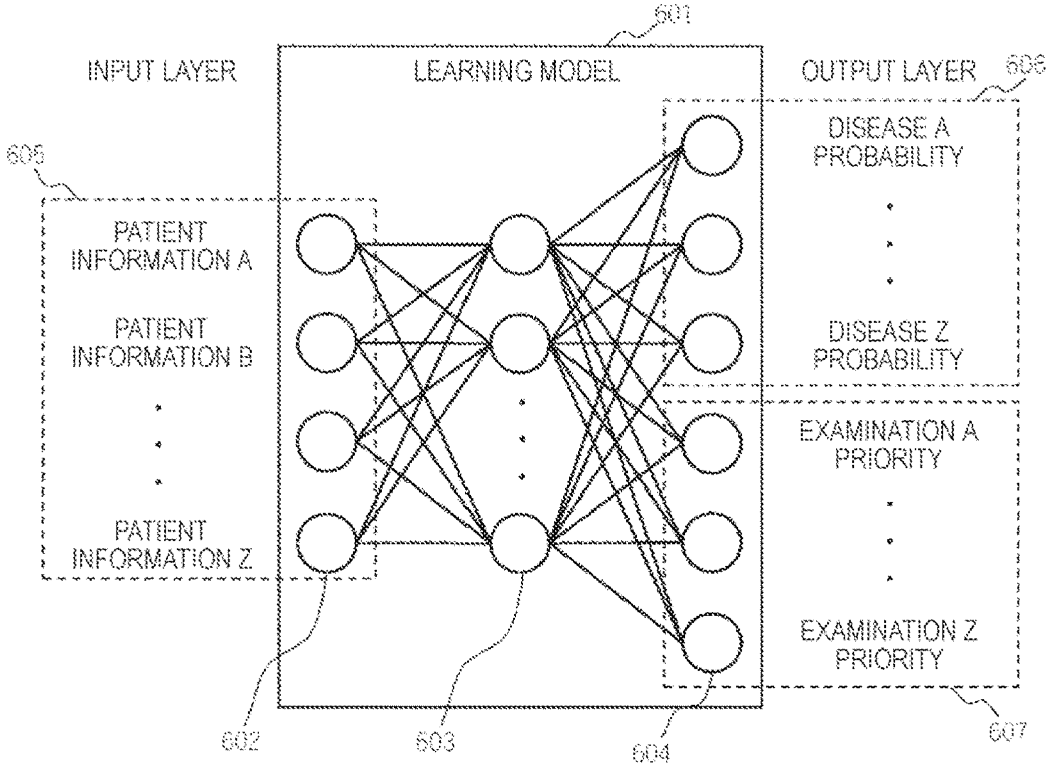
[FIG. 7]
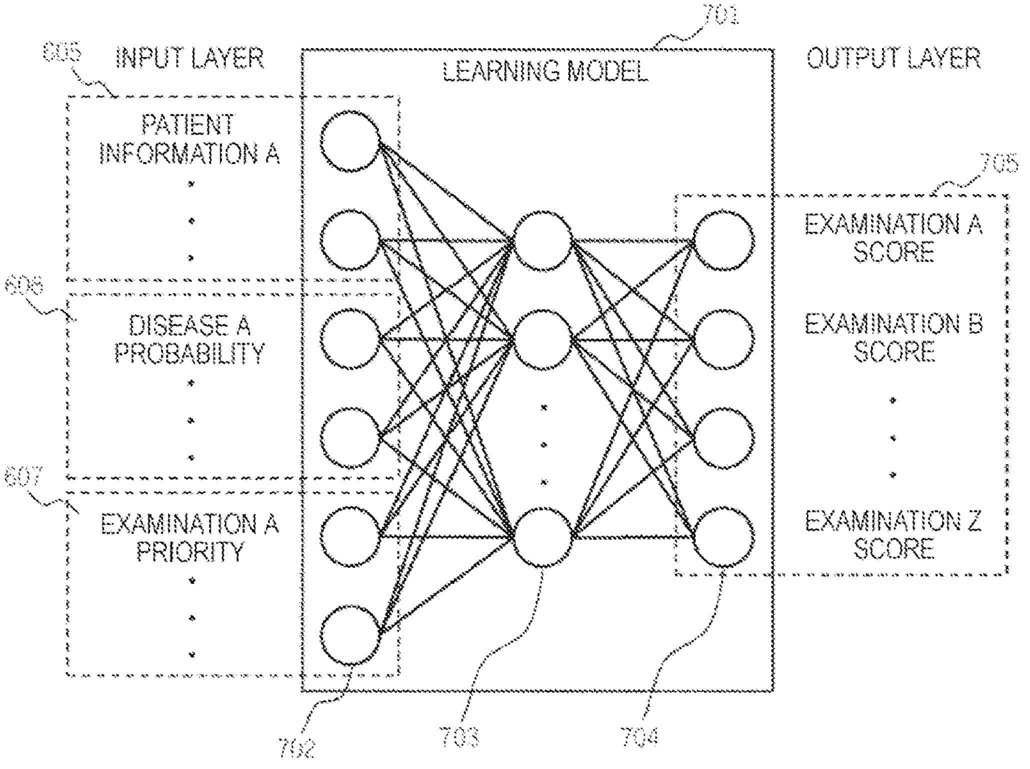

[FIG. 8]
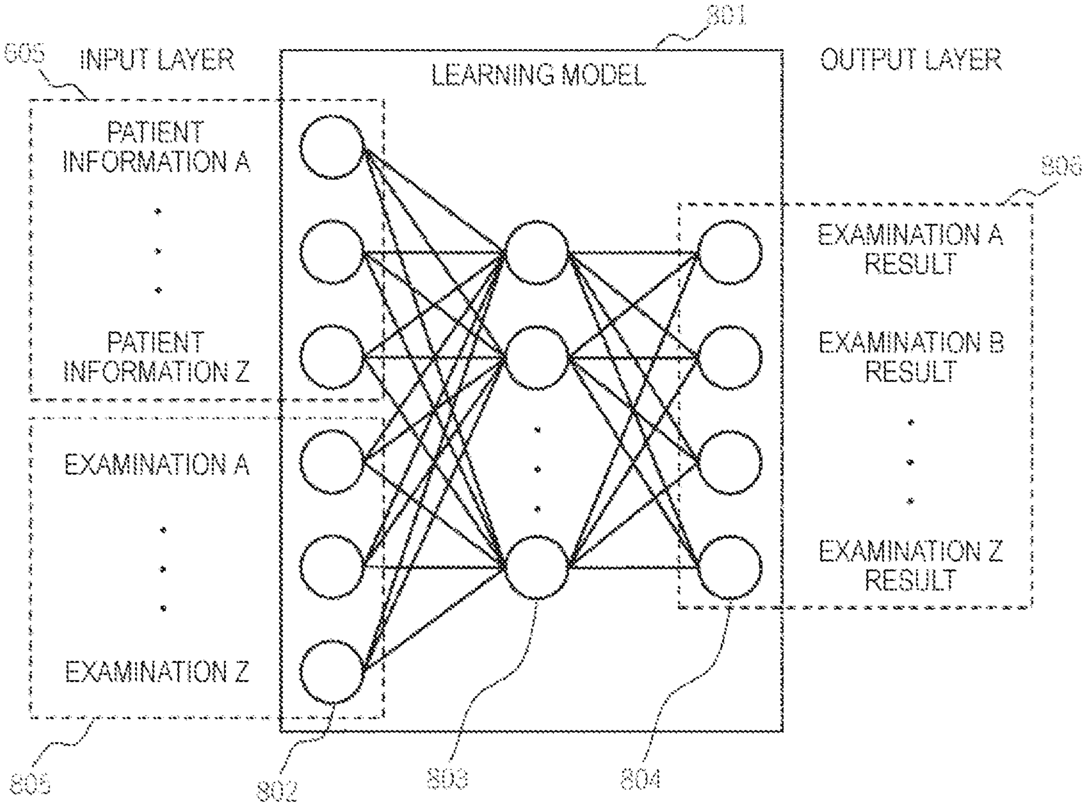

[FIG. 9]
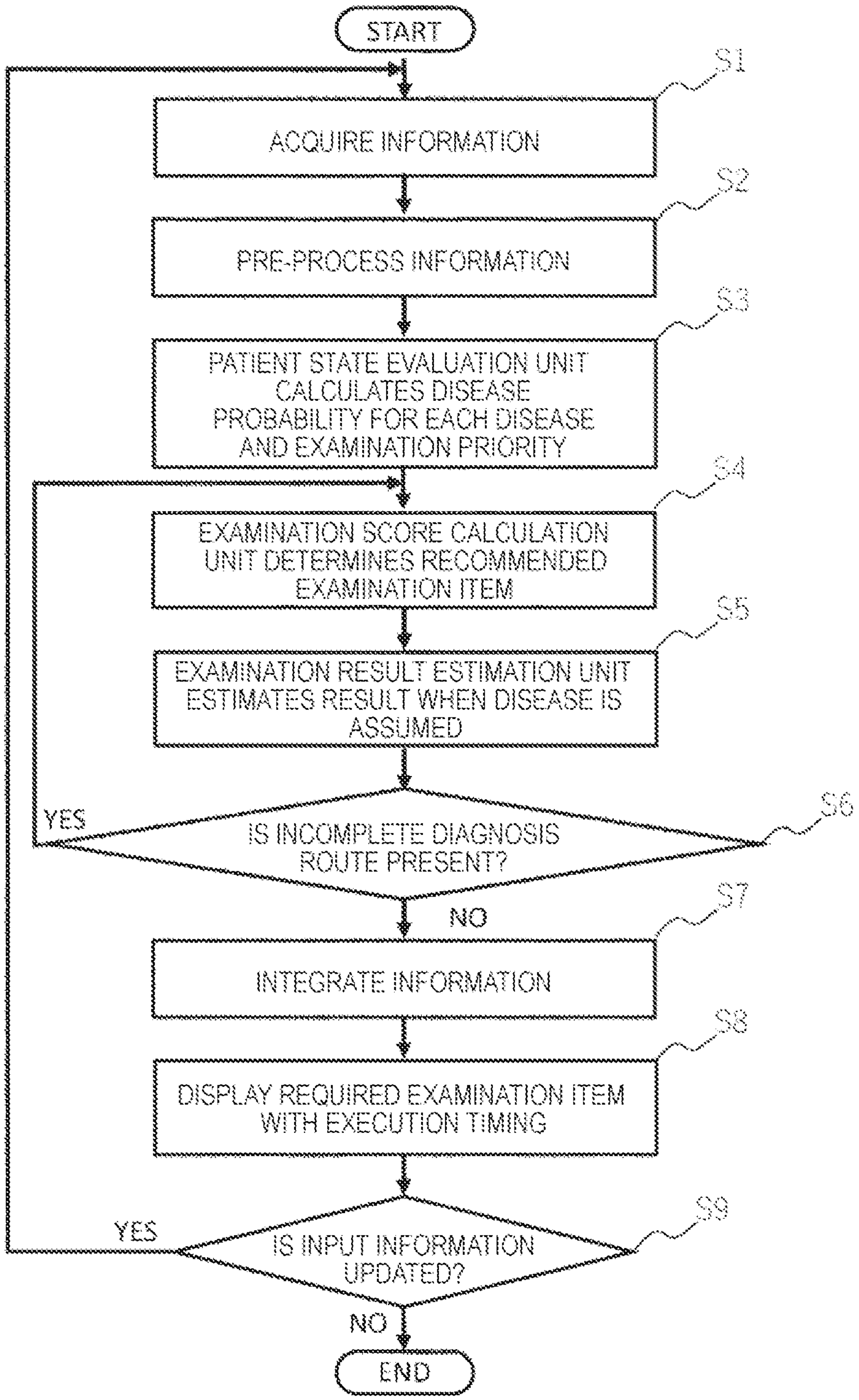

[FIG. 10A]
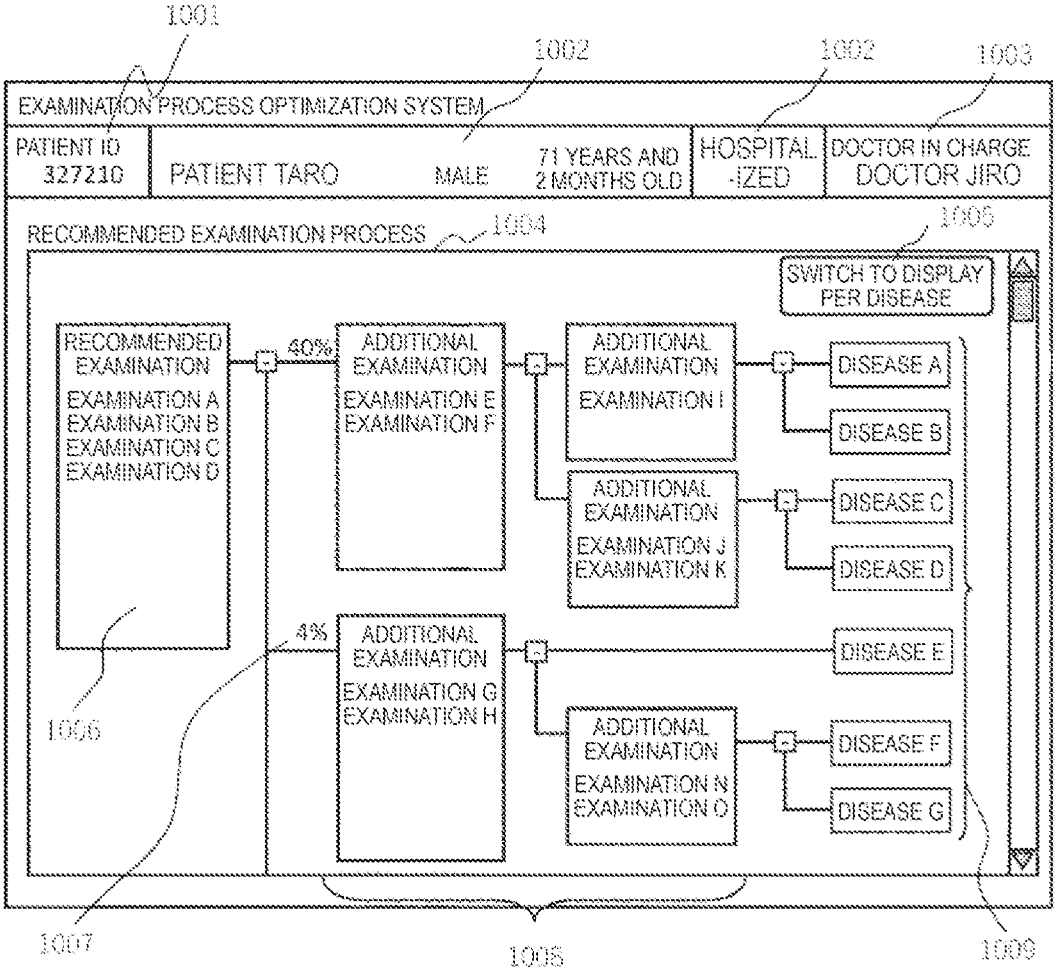

[FIG. 10B]
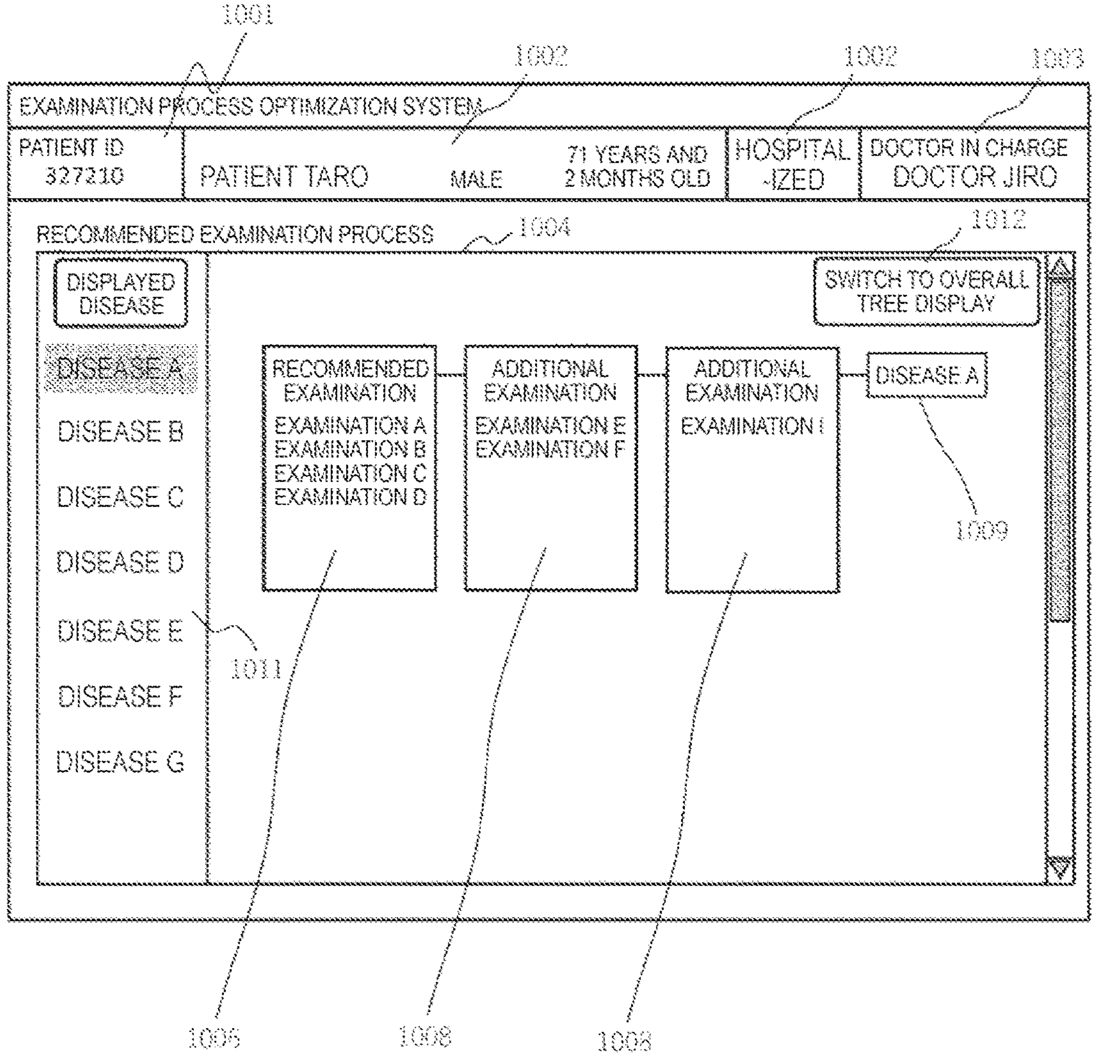

[FIG. 10C]
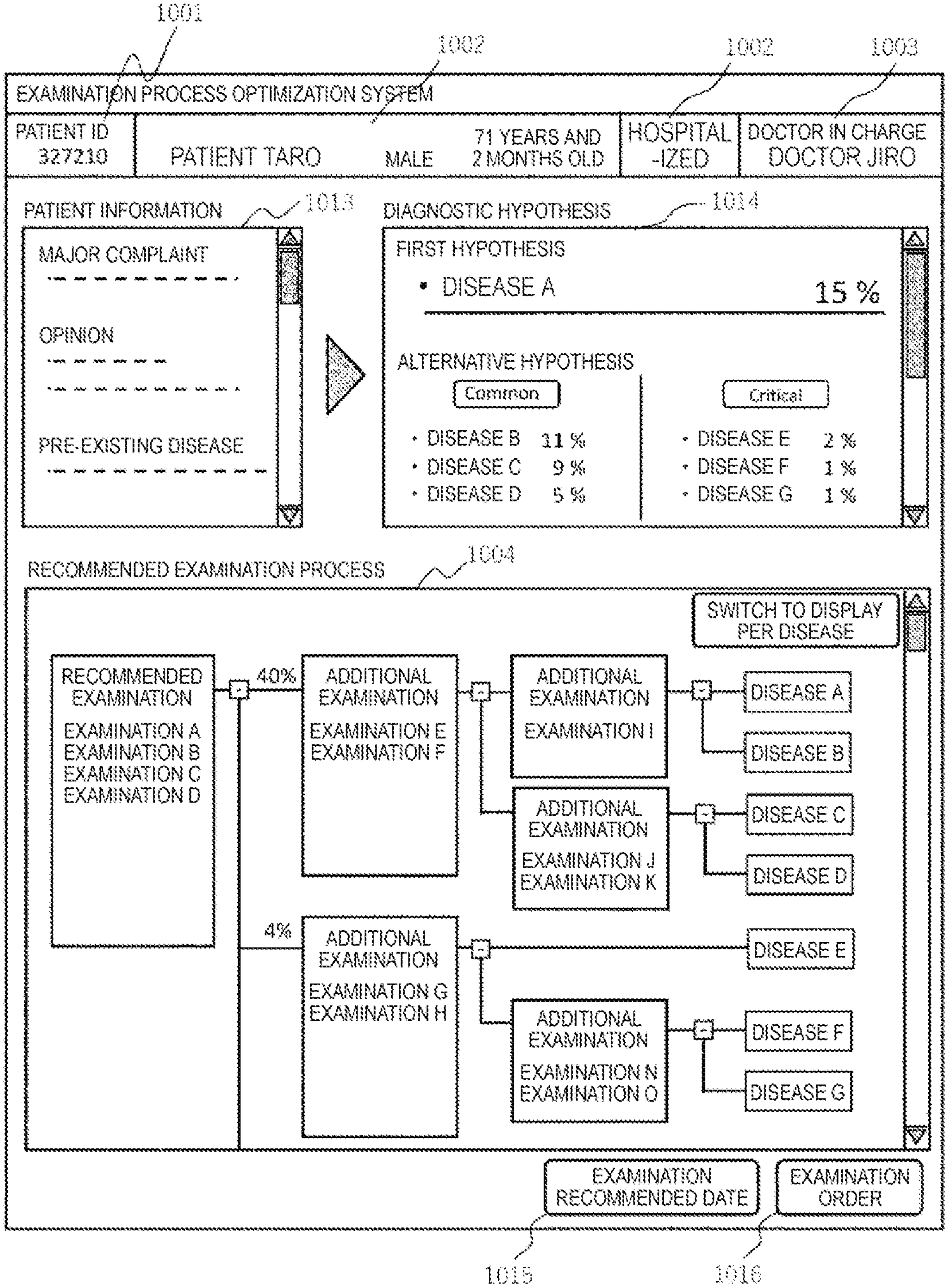

INFORMATION PROCESSING APPARATUS, CLINICAL DIAGNOSIS SYSTEM, AND PROGRAM

TECHNICAL FIELD

The present invention relates to an information processing apparatus, a clinical diagnosis system, and a program.

BACKGROUND ART

In the process of clinical diagnosis, the making of an examination plan that can reduce a burden on a patient as much as possible and uses an examination result for most effectively estimating a disease depends on knowledge and experiences of a doctor. Note that there is also a possibility that an optimum examination plan for a patient cannot be made depending on expertise, a fatigue state, or the like of a doctor in charge. Accordingly, a system that supports clinical diagnosis by providing information useful for determining an examination to be executed to a doctor is proposed. For example, PTL 1 discloses a system that outputs candidates for a disease name that may affect a patient and a subsequent examination to be executed for confirming the disease name based on acquired examination data (For example, ABSTRACT of PTL 1).

CITATION LIST

Patent Literature

PTL 1: JP2020-126284A

SUMMARY OF INVENTION

Technical Problem

However, in the technique described in PTL 1, a doctor can grasp candidates of an examination to be subsequently executed but cannot grasp an overview of examinations required until confirmation of a disease, the overview including a plan of an examination to be executed after the subsequent examination.

An object of the present invention is to provide an information processing clinical diagnosis system, and a program, in which an overview of examinations required until confirmation of a disease can be grasped.

Solution to Problem

To achieve the object, an information processing apparatus according to the present invention includes: an information acquisition unit that acquires patient information; an examination planning unit that specifies an examination item to be executed based on the patient information acquired by the information acquisition unit; and an output unit that outputs the examination item specified by the examination planning unit, in which the output unit outputs a plurality of examination items required until a disease can be confirmed or denied together with execution timings.

Advantageous Effects of Invention

According to the present invention, it is possible to provide an information processing apparatus, a clinical diagnosis system, and a program in which an overview of examinations required until confirmation of a disease can be grasped.

BRIEF DESCRIPTION OF DRAWINGS

FIG. 1 is an overall configuration diagram illustrating a clinical diagnosis system according to an embodiment of the present invention.

FIG. 2 is a diagram illustrating a specific example of accumulated medical information.

FIG. 3 is a diagram illustrating a specific example of an examination characteristic value.

FIG. 4 is a diagram illustrating a specific example of a disease characteristic value.

FIG. 5 is a functional block diagram illustrating an information processing apparatus according to an embodiment of the present invention.

FIG. 6 is a diagram illustrating a learning model in which a patient state evaluation unit evaluates a state of a target patient.

FIG. 7 is a diagram illustrating a learning model in which an examination score calculation unit calculates an examination recommendation score for estimating an optimum examination for the target patient at a current timing.

FIG. 8 is a diagram illustrating a learning model in which an examination result estimation unit estimates an examination result.

FIG. 9 is an example of a flowchart illustrating a process in the clinical diagnosis system according to the present embodiment.

FIG. 10A is a first screen example output from an output unit of the information processing apparatus.

FIG. 10B is a second screen example output from the output unit of the information processing apparatus.

FIG. 10C is a third screen example output from the output unit of the information processing apparatus.

DESCRIPTION OF EMBODIMENTS

An embodiment of the present invention will be described below using the drawings.

In the present specification, a disease is a collective term for a bad condition felt by a patient, an illness, a sickness, a syndrome, a disability, an underlying disease, a pre-existing disease, and the like, and is not limited to a disease handled by a specific diagnosis and treatment department. An examination is a collective term for all the means for acquiring body information of a patient in a medical institution. Specific examples of the examination include general clinical examination, hematological examination, biochemical examination, immunoserological examination, microbiological examination, histopathological examination, cytodiagnosis, vital function examination, endoscopic examination, imaging examination, history taking, medical questionnaire, questions in a medical interview, precautions in a medical interview, acquisition items in physical findings, acquisition methods in physical findings, rounds, medication, treatment, surgery, general medical check-up, multiphasic health screening, and other medical actions. Acquirers of information are not limited to doctors and include medical workers or other staff members belonging to medical institutions and patients or persons relating to the patients. Patient information is a collective term for all pieces of information relating to a patient acquired in a medical institution. Specific examples of the patient information include age, gender, major complaint, opinion, symptom, past history, family history, examination items executed on a patient, treatment history, medication information, various examination results, and information regarding other medical actions.

FIG. 1 is an overall configuration diagram illustrating a clinical diagnosis system according to the embodiment. As illustrated in FIG. 1, the clinical diagnosis system according to the present embodiment is configured by an information processing apparatus 101 and a medical information server 117 connected to the information processing apparatus 101.

The information processing apparatus 101 includes an arithmetic device 102, a main storage device 103, an input unit 104, an output unit 105, a communication unit 106, and an auxiliary storage device 107.

The arithmetic device 102 is a device that executes programs read to the main storage device 103 and is, for example, a central processing unit (CPU) or a graphics processing unit (GPU). The main storage device 103 is a device that stores programs to be executed, information to be processed, and information including a process result.

The input unit 104 is a device that inputs information to the information processing apparatus 101 or the medical information server 117 and is, for example, a device such as a keyboard or a mouse.

The output unit 105 is a device that outputs a process result by the clinical diagnosis system and is, for example, a device such as a monitor or a printer.

The communication unit 106 is a device that transmits and receives data to and from external devices including an external server or an external DB via a communication network and is, for example, a network interface.

The auxiliary storage device 107 is a device that stores information including a program storage unit 108, a learning model storage unit 109, and an accumulated information storage unit 113 and is, for example, a non-volatile storage medium such as a hard disk drive (HDD) or a solid state drive (SSD).

The program storage unit 108 is an area that stores various programs for implementing optimization of an examination process in the clinical diagnosis system according to the present embodiment. The learning model storage unit 109 stores a learning model including a patient state evaluation unit 110, an examination score calculation unit 111, and an examination result estimation unit 112. The patient state evaluation unit 110, the examination score calculation unit 111, and the examination result estimation unit 112 will be described in detail using FIGS. 6, 7, and 8, respectively. The accumulated information storage unit 113 stores information including an examination characteristic value 114, a disease characteristic value 115, and accumulated medical information 116 as information used for optimization of an examination process in the clinical diagnosis system according to the present embodiment. The examination characteristic value 114, the disease characteristic value 115, and the accumulated medical information 116 will be described in detail using FIGS. 2, 3, and 4, respectively.

The medical information server 117 includes electronic medical record information 118, guideline information 119, receipt information 120, and an examination ordering system 121.

The electronic medical record information 118 records a medical treatment process and the like that are executed on a patient, and by referring to the data, a doctor can grasp all pieces of information obtained from a patient at the moment. The information recorded in the electronic medical record information 118 includes information that is generated by a medical institution, a health organization, or an individual patient to grasp a state of a patient such as a diagnosis and treatment record, a medical questionnaire, a hospital journal, medical treatment journals from each department, a prescription, an operative record, a nursing record, a book that clarifies the number of hospitalized patients, a book that clarifies the number of outpatients, or a hospitalization treatment plan.

The guideline information 119 records guidelines to which doctors or other medical workers refer for medical treatments. The information recorded in the guideline information 119 includes various guidelines such as medical guidelines proposed from organizations such as each of institutes, or in-hospital regulations and in-hospital guidelines in each of hospitals.

The receipt information 120 records a receipt including information for a health insurance treatment that is executed on a patient enrolled in a health insurance such as personal information of the patient, a diagnosis and treatment department where the patient took a treatment, a disease name, or a treatment such as a surgery, an examination, or a rehabilitation that is executed on the patient.

The examination ordering system 121 is a system that smoothly transmits an instruction of a doctor to each of departments of a hospital, and has a function of a support system for an order such as a prescription, an examination, a meal, or a reservation, a reservation management function of an examination, or a treatment planning function.

Next, the accumulated medical information 116 will be described. FIG. 2 is a diagram illustrating a specific example of the accumulated medical information. As illustrated in FIG. 2, the accumulated medical information 116 is information recorded as data of past cases, and includes a patient number 201, a confirmed diagnosis 202, and an examination 203. The patient number 201 is identification information for uniquely identifying a patient. The confirmed diagnosis 202 records a disease name of each of patients that is finally confirmed. The examination 203 includes a result of each of examinations that are executed on a patient, for example, an examination A 204 or an examination B. The examination A 204 includes a date and time 205, an item 206, and a result 207. The date and time 205 is a date and time on which an examination is executed or a date and time on which an examination result is acquired, and is information that specifies the time when the examination is executed on a patient. The item 206 is information for specifying an examination item to be executed on a patient. The result 207 is information for specifying a result obtained by executing an examination.

Next, the examination characteristic value will be described. FIG. 3 is a diagram illustrating a specific example of the examination characteristic value. As illustrated in FIG. 3, the examination characteristic value 114 includes an examination item 301, a reference value 302, a cost 303, a positive likelihood ratio 304, and a negative likelihood ratio 305.

The examination item 301 is information for specifying an examination that is executed in a medical institution such as a hospital.

The reference value 302 is information of a reference value that is set in each of examination items. The reference value is generally set as a 95% range in the middle of an examination value distribution of able-bodied people, and is used as a reference for determining an examination value. The reference value does not need to be set for each of examinations.

The cost 303 is a value that is comprehensively calculated from information such as an insurance score or a document regarding the degree of invasion of an examination.

In the positive likelihood ratio 304, a value is set for each of diseases, and the positive likelihood ratio 304 is information regarding a numerical value representing how much a person with a disease is more likely to be positive than a person without a disease for each of examinations. When the positive likelihood ratio 304 varies depending on examination results, the positive likelihood ratio 304 is recorded for each of the examination results. For example, the positive likelihood ratio 304 is set to vary between a case where a difference from the reference value is large and a case where a difference from the reference value is small.

In the negative likelihood ratio 305, a value is set for each of diseases, and the negative likelihood ratio 305 is information regarding a numerical value representing how much a person with a disease is more likely to be negative than a person without a disease for each of examinations. When the negative likelihood ratio 305 varies depending on examination results, the negative likelihood ratio 305 is recorded for each of the examination results. Note that, for example, when correlation between an examination and a disease is little, the value of the positive likelihood ratio 304 or the negative likelihood ratio 305 does not need to be set.

Next, the disease characteristic value 115 will be described. FIG. 4 is a diagram illustrating a specific example of the disease characteristic value. As illustrated in FIG. 4, the disease characteristic value 115 includes a disease name 401, a condition 402, a pretest probability 403, an examination threshold 404, a treatment threshold 405, and a risk score 406.

The disease name 401 records the name of a disease set from the accumulated medical information or various documents and the like.

The condition 402 is an identifier for recording a value for each of conditions when the value of the pretest probability 403, the examination threshold 404, the treatment threshold 405, or the risk score 406 varies depending on conditions for the same disease. Examples of conditions recorded in the condition 402 include age, past history, medication information, gender, and family history. A combination of the examples may be recorded as the condition.

The pretest probability 403 is a set value of a disease probability assumed before executing various examinations on a patient. The value is calculated from the accumulated medical information, epidemiological data, clinical study data, or data such as an empirical rule of a doctor. A method of expressing the pretest probability 403 may be odds.

The examination threshold 404 (second threshold) is a reasonable probabilistic threshold that is preset for each of diseases and is a reference for denial of a disease. When the disease probability is equal to the examination threshold 404 or higher, it can be considered that the disease is sufficiently suspicious for executed an examination and the examination should start even when considering a disadvantage (a load on the patient, and the like) of the examination. The value is calculated from the accumulated medical information, epidemiological data, clinical study data, or data such as an empirical rule of a doctor by comprehensively evaluating various data such as the risk of the disease, the prognosis of the patient, or the risk of the examination.

The treatment threshold 405 (first threshold) is a reasonable probabilistic threshold that is preset for each of diseases and is a reference for confirmation of a disease, and is a value higher than the examination threshold 404. When the disease probability is equal to the treatment threshold 405 or higher, it can be considered that one disease is confirmed and the treatment may start. The value is calculated from the accumulated medical information, epidemiological data, clinical study data, or data such as an empirical rule of a doctor by comprehensively evaluating various data such as the risk of the disease, the risk of the treatment, or the cost of the treatment.

For example, when a disease A is a cold, an examination such as auscultation that is executed in an examination room has a relative small burden on a patient as compared to an advantage for the patient obtained by the examination. Therefore, the examination threshold 404 is set to be low. A disadvantage obtained when the treatment starts to be executed on a patient who does not have a cold is relatively small as compared to an advantage obtained when the treatment is executed on a patient who does have a cold. Therefore, the treatment threshold 405 is also set to be small.

The risk score 406 is a value that is set for evaluating the risk of each of diseases by comprehensively evaluating the fatality of the disease, the exacerbation rate, and the prognosis of the patient.

Next, a configuration of the information processing apparatus 101 according to the present embodiment will be described. FIG. 5 is a functional block diagram illustrating the information processing apparatus according to the embodiment. As illustrated in FIG. 5, the information processing apparatus 101 includes the accumulated information storage unit 113, an input information acquisition unit 505, an information pre-processing unit 506, a characteristic information acquisition unit 507, a learning model 508, an examination planning unit 509, and the output unit 105.

Each of the functions of the information processing apparatus 101 is executed by the arithmetic device 102 executing programs stored in the auxiliary storage device 107 such that a predetermined process is implemented in cooperation with another hardware. The program may be provided by being incorporated into the auxiliary storage device 107 or the main storage device 103 in advance. The program may be provided by being recorded in a recording medium that is readable by the information processing apparatus 101 such as a CD-ROM in the form of an installable or executable file. The program can also be downloaded from a computer connected via the communication unit 106 to be installed in the main storage device 103 or the auxiliary storage device 107.

Input information 501 includes medical record information 502, in-hospital information 503, and operation information 504. The medical record information 502 is medical information regarding a patient that is recorded by a doctor in a medium such as a diagnosis and treatment record. The doctor can grasp information including a body state of a patient by referring to the medical record information. The medical record information 502 may be sequentially updated during a treatment of a patient, when acquiring an examination result, or at other stages. The in-hospital information 503 is information stored in the medical information server 117, and includes information such as the guideline information 119, the receipt information 120, and the examination ordering system 121. A doctor or a medical worker can grasp a date on which an examination is executable, an execution status, the number of outpatients, or a guideline of an examination from the information, and can select an examination item or can set a specific date and time of an examination according to the information. The operation information 504 is input information from the input unit 104 or the like, and is information regarding an operation including a display switch of a screen or a change in display content.

The input information acquisition unit 505 has a function of extracting information required for a process from the input information 501.

The information pre-processing unit 506 has a function of integrating the acquired information into a form that can be input to the learning model 508.

The characteristic information acquisition unit 507 has a function of extracting each piece of information stored in the accumulated information storage unit 113 according to the information obtained by the input information acquisition unit 505.

The learning model 508 includes the patient state evaluation unit 110, the examination score calculation unit 111, and the examination result estimation unit 112. The information processed by the information pre-processing unit 506 is applied to the learning model 508. The patient state evaluation unit 110, the examination score calculation unit 111, and the examination result estimation unit 112 will be described in detail using FIGS. 6 to 8.

The examination planning unit 509 has a function of specifying an examination item to be executed and generating a data format for display to a user based on the patient information acquired through the input information acquisition unit 505, each of the characteristic values acquired through the characteristic information acquisition unit 507, and the information calculated by the learning model 508.

The output unit 105 has a function of displaying the information generated by the examination planning unit 509 to the user.

Next, the patient state evaluation unit 110 of the information processing apparatus according to the present embodiment will be described. FIG. 6 is a diagram illustrating a learning model in which the patient state evaluation unit evaluates a state of a target patient. A learning model 601 is a model that learns to output a disease probability 606 and an examination priority 607 in response to information including patient information 605 as inputs. The patient information 605 is information obtained from the patient by examinations that has been executed thus far. The disease probability 606 is an index representing a probability that a target patient has each of diseases. The examination priority 607 is an index that is calculated from information including the risk of a disease and the level of the disease probability 606 and represents the degree to which an examination is preferentially executed.

The learning model 601 includes an input layer 602, an intermediate layer 603, and an output layer 604. The input layer 602, the intermediate layer 603, and the output layer 604 include a plurality of input units, a plurality of intermediate units, and a plurality of output units, respectively, which are represented by circles in FIG. 6. In FIG. 6, the intermediate layer 603 is a single layer but may be a plurality of layers. Information input to the input layer 602 is added and input to the intermediate layer 603 according to a weighting coefficient generated in the learning process of the learning model 601. Information input to the intermediate layer 603 is also added and output to the output layer 604 according to the weighting coefficient. Accordingly, the learning model 601 can be considered to be a process of nonlinearly converting a value input to the input layer 602 and outputting the converted value to the output layer 604.

Next, the examination score calculation unit 111 of the information processing apparatus according to the present embodiment will be described. FIG. 7 is a diagram illustrating a learning model in which the examination score calculation unit calculates an examination recommendation score for estimating an optimum examination for the target patient at a current timing. A learning model 701 is a model that learns to output an examination recommendation score 705 in response to information including the patient information 605, the disease probability 606, and the examination priority 607 as inputs.

The learning model 701 includes an input layer 702, an intermediate layer 703, and an output layer 704. The input layer 702, the intermediate layer 703, and the output layer 704 are the same as the input layer 602, the intermediate layer 603, and the output layer 604 in the learning model 601, and thus the description thereof will not be made.

Next, the examination result estimation unit 112 in the learning model of the information processing apparatus according to the present embodiment will be described. FIG. 8 is a diagram illustrating a learning model in which the examination result estimation unit estimates an examination result. A learning model 801 is a model that learns to output an estimated examination result 806 in response to the patient information 605 and an executed examination item 805 as inputs. The executed examination item 805 is an examination item to be executed on a patient that is determined based on information including the examination recommendation score 705. The estimated examination result 806 is an examination result that is estimated when the executed examination item 805 is executed assuming that the target patient has a specific disease. The assumed disease may be only a disease having high importance from the information including the disease probability 606 and the examination priority 607 or may be determined using another method.

The learning model 801 includes an input layer 802, an intermediate layer 803, and an output layer 804. The input layer 802, the intermediate layer 803, and the output layer 804 are the same as the input layer 602, the intermediate layer 603, and the output layer 604 in the learning model 601, and thus the description thereof will not be made.

As the learning model of the patient state evaluation unit 110 illustrated in FIG. 6, the learning model of the examination score calculation unit 111 illustrated in FIG. 7, and the learning model of the examination result estimation unit 112 illustrated in FIG. 8, any learner such as linear regression, logistic regression, support vector machine, decision tree, Random forest, neural network, or naive bayes can be used.

Next, the flow of a process relating to optimization of the examination process in the clinical diagnosis system according to the present embodiment will be described. FIG. 9 is an example of a flowchart illustrating the process in the clinical diagnosis system according to the present embodiment.

The process is executed by a program stored in the program storage unit 108 of the information processing apparatus 101, and is implemented by cooperation of hardware of the information processing apparatus 101 and the medical information server 117.

(Step S1) The input information acquisition unit 505 acquires the input information 501, and the characteristic information acquisition unit 507 acquires the examination characteristic value 114, the disease characteristic value 115, and the accumulated medical information 116 stored in the accumulated information storage unit 113. In addition to the operation information 504, the input information acquisition unit 505 acquires the medical record information 502 or the in-hospital information 503 (including the guideline information 119 or the receipt information 120) stored in the medical information server 117.

(Step S2) The information pre-processing unit 506 receives the information acquired by the input information acquisition unit 505 and the characteristic information acquisition unit 507, generates the patient information, and executes pre-processing such as processing of information. The pre-processing of the information pre-processing unit 506 includes a process of analyzing and decomposing text data described in an electronic medical record or an interpretation report into category data or numerical value data, a process of adding the examination characteristic value 114 or the disease characteristic value 115 in the accumulated information storage unit 113 to the patient information, a state of a hospital, or information of a doctor in charge and adjusting the information, and a process of converting extracted data into a data format that can be input to the learning model.

(Step S3) The patient state evaluation unit 110 acquires a data set regarding the patient information generated in Step S2 from the information pre-processing unit 506, and calculates the possibility that each of diseases is subjected to be suspicious (disease probability) and the priority in which a test by an examination is recommended (examination priority). The examination priority is calculated based on the possibility that the patient has a given disease, the risk score 406 in the disease characteristic value 115, and the like. Target examinations for which the priority is calculated are all the examinations required until a disease where the current disease probability is equal to the examination threshold 404 or higher is confirmed or denied in diagnosis.

(Step S4) The examination score calculation unit 111 acquires a data set regarding the patient information generated in Step S2 from the information pre-processing unit 506, acquires the current disease probability and the examination priority generated in Step S3 from the patient state evaluation unit 110, and calculates the examination recommendation score 705. The examination planning unit 509 determines a recommended examination as the examination item to be executed initially (the next timing) based on the examination recommendation score 705.

(Step S5) The examination result estimation unit 112 acquires a data set regarding the patient information generated in Step S2 from the information pre-processing unit 506, acquires a combination of the examinations to be executed from the examination score calculation unit 111, and estimates an examination result assuming that the patient has a given disease.

(Step S6) The examination planning unit 509 determines whether a confirmed diagnosis can be considered as having the disease probability at the moment based on the information acquired from the patient state evaluation unit 110, the examination score calculation unit 111, and the information pre-processing unit 506.

Here, an example of a specific process for specifying examination items required until a disease is confirmed will be described. The patient state evaluation unit 110 calculates an assumed disease probability that is expected after an examination depending on an examination result assuming that the recommended examination item determined in Step S4 is executed. When the assumed disease probability is lower than the treatment threshold 405, the examination planning unit 509 determines that the process is not at a stage where a confirmed diagnosis can be made to start a and treatment, specifies an additional examination item to be executed additionally. The patient state evaluation unit 110 calculates an assumed disease probability that is expected after an examination depending on an n examination result assuming that the additional examination item is executed. When the assumed disease probability is equal to the treatment threshold 405 or higher, the examination planning unit 509 determines that the process may be at a stage where a confirmed diagnosis can be made to start a treatment, and a diagnosis route of the disease ends. In Step S6, the examination planning unit 509 determines whether diagnosis routes of all the diseases are completed, and returns to Step S4 to repeat the same process for a disease of which the diagnosis route is incomplete, that is, a disease where the disease probability is lower than the treatment threshold 405. When the disease probability is lower than the examination threshold 404, the disease can be denied. Therefore, the diagnosis route ends. The index such as the examination threshold 404 or the treatment threshold 405 used by the examination planning unit 509 for the determination may be adjusted depending on conditions such as age.

(Step S7) The examination planning unit 509 integrates information including the patient information generated in Step S2, the disease probability 606 and the examination priority 607 calculated in Step S3, the recommended examination item determined in Step S4, and the diagnosis routes of all the examination items including the additional examination item specified in Step S6, and processes the integrated information into a data set that can be displayed to the user.

(Step S8) The output unit 105 displays the data set formed in Step S7, that is, a plurality of examination items required until a disease can be confirmed or denied together with execution timings. The data set formed in Step S7 may be stored in the accumulated information storage unit 113.

(Step S9) The input information acquisition unit 505 checks whether the input information 501 is updated, and when the update is checked, the input information acquisition unit 505 returns to Step S1, executes the same process according to the updated information, and causes the output unit 105 to display the result. Specifically, when the patient information is updated, for example, by update of the electronic medical record or acquirement of the examination result, or when other pieces of information are updated, the update is reflected on the optimization process of the examination process in real time.

Next, a screen display example that is output from the information processing apparatus according to the present embodiment will be described.

FIG. 10A is a first screen example output from the output unit of the information processing apparatus. Hereinafter, the screen that is displayed to the user through the output unit 105 of the information processing apparatus 101 will be described. However, the corresponding data may be stored in a storage device.

As illustrated in FIG. 10A, the present screen example includes a patient ID 1001, patient information 1002, a doctor-in-charge information 1003, and a recommended examination process 1004.

The patient ID 1001 may display an identifier and a common character string in an electronic medical record system operated by a medical institution or the like, or may display a patient number or the like that can uniquely specify a patient in a medical institution or the like. As a result, the information can be unitarily managed in combination with a system that is already used in a medical institution or the like.

The patient information 1002 is a portion that displays basic information of a patient. In the present screen example, the name of the patient, the gender of the patient, the age of the patient, and whether the patient is an outpatient and a hospitalized patient are displayed. However, other pieces of patient information may be displayed.

The doctor-in-charge information 1003 displays information of a doctor in charge of the treatment of the patient displayed by the patient information 1002. In the screen example of FIG. 10A, the name of the doctor is displayed. However, other pieces of information of the doctor such as specialty may be displayed.

The recommended examination process 1004 includes a display format switch button 1005, a recommended examination 1006, a branching probability 1007, an additional examination 1008, and a confirmed diagnosis 1009, and presents an optimized examination process to the user. In particular, the recommended examination 1006, the additional examination 1008, and the confirmed diagnosis 1009 are output in a tree diagram. Therefore, an execution timing of each of examination items at which a confirmed diagnosis of each of diseases can be made can be comprehensively grasped.

The display format switch button 1005 is a user interface for switching the display format of the recommended examination process 1004. The user can select the display format switch button 1005 by operating the input unit 104 in the information processing apparatus 101.

The recommended examination 1006 is an area that displays one or more examination items to be executed on a patient at the moment. When two or more examination items are displayed, the examination items are examinations to be executed at the same timing and are examinations that should be already ordered before a doctor or another medical worker checks the examination result.

The branching probability 1007 is output to each of branched portions in the tree diagram, and is a value representing what degree with a probability that a pattern of a result obtained by executing the recommended examination 1006 occurs.

The additional examination 1008 displays a recommended examination that is executed at the previous timing, or when an examination item to be executed changes depending on the result of the additional examination, displays recommended examination items that vary. In FIG. 10A, two additional examinations are connected after the recommended examination. The configuration shows that the examination results obtained by initially executing the recommended examination are divided into two patterns and the additional examination to be executed varies depending on the patterns. Here, the examination result that is assumed in each of the patterns estimated by the examination result estimation unit 112 in Step S5 may also be displayed in the branched portion of the tree diagram.

The confirmed diagnosis 1009 is output to a portion corresponding to each of ends of the tree diagram, and is a disease name that is confirmed as a result of executing the recommended examination, or executing the recommended examination and the additional examination. When a plurality of diseases are estimated from the patient information, the confirmed diagnosis 1009 displays names of a plurality of diseases. Regarding the number of displays in the confirmed diagnosis 1009, all the diseases may be displayed, or only some diseases may be displayed. The diseases to be displayed in the confirmed diagnosis 1009 may be selected by weighting based on the index such as the risk score 406 of the disease.

Regarding the information displayed in the recommended examination process 1004, the display content may be updated in synchronization with the timing when the input information 501 is updated. Specifically, when a doctor takes a medical interview of a patient, and the content heard from the patient is filled in an electronic medical record, the updated content is reflected, and the content to be subsequently asked to the patient is displayed as the recommended examination.

FIG. 10B is a second screen example output from the output unit of the information processing apparatus. The second screen example is a screen to be transitioned to when the display format switch button 1005 is selected in FIG. 10A illustrating the first screen example.

As illustrated in FIG. 10B, the present screen example includes the patient ID 1001, the patient information 1002, the doctor-in-charge information 1003, and the recommended examination process 1004. In the first screen example illustrated in FIG. 10A, a plurality of diseases as confirmed diagnosis are displayed, and each of examinations and execution timings thereof are comprehensively displayed as the information for confirming that a patient has each of diseases. On the other hand, in the second screen example illustrated in FIG. 10B, when a specific disease is selected, examination items required until confirmation of the selected disease are output after being distinguished from examination items required until confirmation of another disease.

The recommended examination process 1004 in the present screen example includes the recommended examination 1006, the additional examination 1008, the confirmed diagnosis 1009, a displayed disease 1011, and a display switch button 1012. In the present screen example, only an examination process required for confirmed diagnosis of one specific disease is extracted and displayed. Therefore, when only one disease is focused on, the user grasps the examination process more easily.

The displayed disease 1011 is a user interface for allowing the user to change the confirmed diagnosis 1009 to be displayed. The user operates the input unit 104 in the information processing apparatus 101 and selects a disease in the displayed disease 1011 such that the optimum examination item and the execution timings thereof can be grasped to confirm the selected disease.

The display switch button 1012 is a user interface for switching the display format of the recommended examination process to the first screen example illustrated in FIG. 10A. The user can select the display switch button 1012 by operating the input unit 104 in the information processing apparatus 101.

FIG. 10C is a third screen example output from the output unit of the information processing apparatus. The third screen example is a screen for displaying information including patient information and diagnostic hypotheses estimated from the patient information in addition to the information of FIG. 10A as the first screen example.

As illustrated in FIG. 10C, the present screen includes the patient ID 1001, the patient information 1002, the doctor-in-charge information 1003, detailed patient information 1013, a diagnostic hypothesis 1014, the recommended examination process 1004, an examination recommended date and time button 1015, and an examination order button 1016. In the present screen example illustrated in FIG. 10C, the detailed patient information 1013 and the diagnostic hypothesis 1014 are displayed together with the recommended examination process 1004 such that the user can understand the reason of the proposed examination process and diagnostic inference to be executed by the user itself can also be supported.

The detailed patient information 1013 is an area that displays the patient information that is acquired from the input information 501 and is processed in the information pre-processing unit 506. The detailed patient information 1013 may be displayed in divided classifications and, in the present screen example, is displayed in classifications such as a major complaint, opinion, a pre-existing disease, and the like.

The diagnostic hypothesis 1014 is an area that displays diagnostic hypotheses estimated based on the disease probability and the like calculated by the patient state evaluation unit 110. In the present screen example illustrated in FIG. 10C, as the diagnostic hypothesis 1014, the disease probability of a disease is displayed together with the disease name. An index other than the disease probability may be displayed. For example, using the risk score 406, an index for comprehensively evaluating the possibility and the risk may be displayed. In the present screen example, the estimated diagnostic hypotheses are displayed after being classified into three types including a first hypothesis, an alternative hypothesis "Common", and an alternative hypothesis "Critical". The first hypothesis displays the most suspicious disease from the patient information. The alternative hypothesis "Common" displays diseases having a high probability. The alternative hypothesis "Critical" displays diseases having a particularly high risk among the diseases assumed for the patient. Note that a method of classifying the diagnostic hypotheses may be a method other than the present screen example, and the diagnostic hypotheses may be displayed without being classified.

The examination recommended date and time button 1015 is a user interface for displaying a specific date and time on which the examination execution is recommended for the recommended examination 1006 and the additional examination 1008 displayed in the recommended examination process 1004. When the examination recommended date and time button 1015 is operated through the input unit 104, the output unit 105 is configured to output an examination candidate date based on patient information, disease characteristics, the number of patients, examination device availability information, and the like. The output unit 105 may output a period (interval) between each of examinations instead of the specific examination candidate date.

The examination order button 1016 is a user interface for ordering an examination through the examination ordering system 121 of the medical information server 117 for the recommended examination 1006 and the additional examination 1008 displayed in the recommended examination process 1004. When the examination order button 1016 is operated through the input unit 104, the examination ordering system 121 is configured to reserve an examination item at the timing displayed by the recommended examination process 1004.

In the third screen example illustrated in FIG. 10C, a disease (disease A) having a high priority based on disease information is displayed as the diagnostic hypothesis 1014, and examination items required until confirmation of the disease are displayed on the uppermost stage of the recommended examination process 1004 in preference to examination items required for confirmation of another disease.

As such, in the clinical diagnosis system according to the present embodiment, the user (not only a doctor but also a patient in some cases) can check a subsequent event that is assumed to occur based on the result of each of examinations before the start of the examination process, and the making of an appropriate examination plan can be supported. By displaying the recommended examination item and the additional examination item in a time series in the tree diagram, the user can comprehensively grasp which examination to be executed at which timing in optimum for specifying a disease. The branching of events caused by each of examination results is visualized. Therefore, the reason for executing a clinical examination or the future prediction can be specifically shared between a doctor and a patient, and the understanding of the patient for the examination can also be improved.

The present invention is not limited to the embodiment and includes various modification examples. For example, the embodiments have been described in detail to easily describe the present invention, and the present invention does not necessarily include all the configurations described above.

REFERENCE SIGNS LIST

101: information processing apparatus
102: arithmetic device
103: main storage device
104: input unit
105: output unit
106: communication unit
107: auxiliary storage device
108: program storage unit
109: learning model storage unit
110: patient state evaluation unit
111: examination score calculation unit
112: examination result estimation unit
113: accumulated information storage unit
114: examination characteristic value
115: disease characteristic value
116: accumulated medical information
117: medical information server
118: electronic medical record information
119: guideline information
120: receipt information
121: examination ordering system
505: input information acquisition unit
506: information pre-processing unit
507: characteristic information acquisition unit
509: examination planning unit

The invention claimed is:

1. An information processing apparatus comprising:
a program storage unit storing at least one program;
a learning model storage unit storing at least one learning model;
a processor that executes the at least one program, and
an output unit that outputs a result of the execution by the processor, wherein the processor acquires and pre-processes patient information and inputs the pre-processed patient information into the learning model,
the processor specifies an examination item to be executed for the patient based on information calculated by the learning model,
the learning model includes:
a first learning model that receives the pre-processed patient information as an input and outputs a disease probability and an examination priority;
a second learning model that receives the pre-processed patient information, the disease probability, and the examination priority as inputs and outputs an examination recommendation score; and
a third learning model that receives the pre-processed patient information and the examination item to be executed determined based on the examination recommendation score as inputs and outputs an estimated examination result that is an examination result estimated when the examination item to be executed is executed assuming that the target patient has a specific disease, the output unit displays a timing at which each of a plurality of examination items required until a disease can be confirmed or denied is executed in a time series on a first display screen, the output unit displays the plurality of examination items in a tree diagram, displays a branching probability in each of branched portions of the tree diagram, and displays a confirmed disease in a portion corresponding to each of ends of the tree diagram, and the output unit displays a display format switch button for switching between the first screen and a second screen that, when a specific disease is selected, the output unit displays examination items required until confirmation of the selected specific disease in a manner that is distinguished from examination items required until confirmation of other diseases.

2. The information processing apparatus according to claim 1, wherein the output unit displays an assumed examination result in each of the branched portions of the tree diagram.

3. The information processing apparatus according to claim 1, wherein the output unit displays a disease having a high priority based on the pre-processed patient information, and displays examination items required until confirmation of the disease in a time series in preference to examination items required until confirmation of other diseases.

4. The information processing apparatus according to claim 1, wherein the processor is further configured to calculate a disease probability for each of a plurality of diseases based on the pre-processed patient information, the storage unit stores a first threshold that is preset for each of the plurality of diseases and is a reference for confirmation of a disease, the processor is further configured to:

specify a recommended examination item to be subsequently executed based on a current disease probability;

calculate an assumed disease probability that is expected after an examination depending on an examination result assuming that the recommended examination item is executed; and when the assumed disease probability is lower than the first threshold, specify an additional examination item to be additionally executed, and the output unit displays the recommended examination item and the additional examination item in a time series.

5. The information processing apparatus according to claim 4, wherein the storage unit also stores a second threshold that is a threshold lower than the first threshold, is preset for each of the diseases, and is a reference for denial of a disease, and the processor is further configured to specify the recommended examination item or the additional examination item until the assumed disease probability is equal to the first threshold or higher for all of diseases for which the current disease probability is equal to the second threshold or higher.

6. A clinical diagnosis system comprising:

the information processing apparatus according to claim 1; and a medical information server that is connected to the information processing apparatus and executes reservation management of an examination, wherein the output unit displays an examination candidate date specified based on an examination device availability or the number of patients received from the medical information server.

7. A clinical diagnosis system comprising:

the information processing apparatus according to claim 1; and a medical information server that is connected to the information processing apparatus and executes reservation management of an examination, wherein the medical information server reserves the examination item at a timing indicated by the output unit.

* * * * *